United States Patent [19]

Plueddemann et al.

[11] Patent Number: 4,866,192

[45] Date of Patent: Sep. 12, 1989

[54] ORGANOSILICON QUATERNARY AMMONIUM ANTIMICROBIAL COMPOUNDS

[75] Inventors: Edwin P. Plueddemann, Midland; Anthony Revis, Freeland, both of Mich.

[73] Assignee: Dow Corning Corporation, Midland, Mich.

[21] Appl. No.: 182,698

[22] Filed: Apr. 18, 1988

[51] Int. Cl.$^4$ ................................................ C07F 7/10
[52] U.S. Cl. ...................................... 556/410; 556/418; 556/424
[58] Field of Search .................... 556/424, 410, 418

[56] References Cited

U.S. PATENT DOCUMENTS

| 3,560,385 | 2/1971 | Roth | 252/49.6 |
|---|---|---|---|
| 3,730,701 | 5/1973 | Isquith et al. | 71/67 |
| 3,794,736 | 2/1974 | Abbott et al. | 424/78 |
| 3,817,739 | 6/1974 | Abbott et al. | 71/67 |
| 3,860,709 | 1/1975 | Abbott et al. | 424/184 |
| 3,865,728 | 2/1975 | Abbott et al. | 210/169 |
| 4,259,103 | 3/1981 | Malek et al. | 71/67 |
| 4,282,366 | 8/1981 | Eudy | 556/413 |
| 4,371,577 | 2/1983 | Sato et al. | 428/96 |
| 4,394,378 | 7/1983 | Klein | 556/413 |
| 4,395,454 | 7/1983 | Baldwin | 428/290 |

FOREIGN PATENT DOCUMENTS

| 156809 | 3/1985 | Japan . |
| 86/01457 | 1/1987 | PCT Int'l Appl. . |
| 1386876 | 3/1975 | United Kingdom . |
| 1433303 | 4/1976 | United Kingdom . |

Primary Examiner—Paul F. Shaver
Assistant Examiner—Stuart L. Hendrickson
Attorney, Agent, or Firm—Jim DeCesare

[57] ABSTRACT

Organosilicon quaternary ammonium antimicrobial compounds are described, particularly, ammonium chloride derivatives of multifunctional diamino quaternary salts, and salts containing a combination of amino, ester, and fluoroalkyl, functionality.

11 Claims, No Drawings

ORGANOSILICON QUATERNARY AMMONIUM ANTIMICROBIAL COMPOUNDS

BACKGROUND OF THE INVENTION

This invention relates to antimicrobial agents and more particularly to new quaternary ammonium salt compounds having biological activity.

Antimicrobial agents are chemical compositions that are used to prevent microbiological contamination and deterioration of products, materials, and systems. Particular areas of application of antimicrobial agents and compositions are, for example, cosmetics, disinfectants, sanitizers, wood preservation, food, animal feed, cooling water, metalworking fluids, hospital and medical uses, plastics and resins, petroleum, pulp and paper, textiles, latex, adhesives, leather and hides, and paint slurries. Of the diverse categories of antimicrobial agents and compositions, quaternary ammonium compounds represent one of the largest of the classes of antimicrobial agents in use. At low concentrations, quaternary ammonium type antimicrobial agents are bacteriostatic, fungistatic, algistatic, sporostatic, and tuberculostatic. At medium concentrations they are bactericidal, fungicidal, algicidal, and viricidal against lipophilic viruses. Silicone quaternary ammonium salt compounds are well known as exemplified by U.S. Pat. No. 3,560,385, issued Feb. 2, 1971, and the use of such compounds as antimicrobial agents is taught, for example, in a wide variety of patents such as U.S. Pat. Nos. 3,730,701, issued May 1, 1973, and 3,817,739, issued June 18, 1974, where the compounds are used to inhibit algae; 3,794,736, issued Feb. 26, 1974, and 3,860,709, issued Jan. 14, 1975, where they are employed for sterilizing or disinfecting a variety of surfaces and instruments; 3,865,728, issued Feb. 11, 1975, where the compounds are used to treat aquarium filters; 4,259,103, issued Mar. 31, 1981; and in British Pat. No. 1,386,876, of Mar. 12, 1975. Published unexamined European Application No. 228464 of July 15, 1987, teaches that microorganisms on plants can be killed by the application thereto of an aqueous mixture of a surfactant and an organosilicon quaternary ammonium compound. In a particular application of an antimicrobial silicone quaternary ammonium compound, a paper substrate is rendered resistant to the growth of microorganisms in U.S. Pat. No. 4,282,366, issued Aug. 4, 1981. In U.S. Pat. No. 4,504,541, issued Mar. 12, 1985, an antimicrobial fabric is disclosed which is resistant to discoloration and yellowing by treatment of the fabric with a quaternary ammonium base containing an organosilicone. U.S. Pat. No. 4,615,937, issued Oct. 7, 1986, as well as its companion U.S. Pat. No. 4,692,374, issued Sept. 8, 1987, relate to wet wiper towelettes having an antimicrobial agent substantive to the fibers of the web and being an organosilicon quaternary ammonium compound. In a series of Burlington Industries, Inc. U.S. Pat. Nos. 4,408,996, issued Oct. 11, 1983, 4,414,268, issued Nov. 8, 1983, 4,425,372, issued Jan. 10, 1984, and 4,395,454, issued July 26, 1983, such compounds are disclosed to be useful in surgical drapes, dressings, and bandages. This same assignee also discloses these compounds as being employed in surgeons' gowns in U.S. Pat. Nos. 4,411,928, issued Oct. 25, 1983, and 4,467,013, issued Aug. 21, 1984. Organosilicon quaternary ammonium compounds have been employed in carpets, in U.S. Pat. No. 4,371,577, issued Feb. 1, 1983; applied to walls, added to paints, and sprayed into shoes, in U.S. Pat. No. 4,394,378, issued July 19, 1983; applied to polyethylene surfaces and used in pillow ticking in U.S. Pat. No. 4,721,511, issued Jan. 26, 1988; in flexible polyurethane foams of fine-celled, soft, resilient articles of manufacture in U.S. Pat. No. 4,631,297, issued Dec. 23, 1986; and mixed with a surfactant in Japanese Kokai Application No. 58-156809, filed Aug. 26, 1983, of Sanyo Chemical Industries, Ltd., for the purpose of achieving uniformity of distribution of the compounds to a surface. Thus, the versatility of such compositions is readily apparent. However, no one, as far as is known, has disclosed an organosilicon quaternary ammonium compound of the group of new compounds in accordance with the present invention and having utility as antimicrobially effective agents. The group of new compositions of the present invention act in preventing microbiological contamination and deterioration, and the new and heretofore undisclosed group of novel compositions set forth in the present invention possess unique features and advantages over existing antimicrobial treating agents and provide improved results thereover. Thus, the existing disadvantages of the prior art compounds are overcome with the present invention wherein improved and new antimicrobial agents are provided.

SUMMARY OF THE INVENTION

This invention relates to a group of new compounds represented by one of the following formulas:

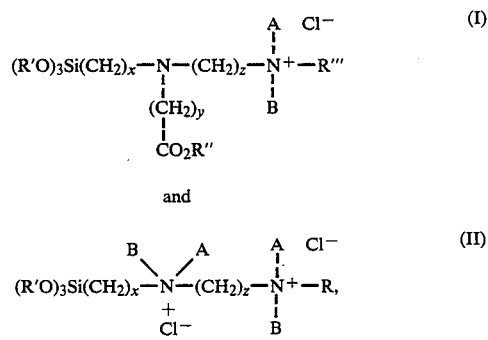

wherein
A and B are each independently selected from methyl, ethyl, and propyl radicals;
R' is selected from methyl, ethyl, propyl, iso-propyl, and butyl radicals;
R" is selected from benzyl, $CF_3(CF_2)_x-$, $CH_{18}H_{37}$, $CF_3(CH_2)_x-$, $-(CH_2)_xSiR'_u(OR')_vR$, alkyl, alkenyl, aryl, and arylalkyl radicals;
R'" is $CH_2-G$ wherein
G is selected from R', R", ethers, ketones, esters, or $CO_2R$ groups;
u has a value of from 0 to 2;
v has a value of from 0 to 2 with the proviso that u+v cannot exceed 2;
x has a value of from 0 to 18;
y has a value of 2;
z has a value of from 2 to 18; and
R is selected from R', R", or R'".

Representative of such category of new compounds and to which the herein disclosed invention relates can be named, for example:
Dimethyl-2-(dimethylamino)ethyl-3-(trimethoxysilyl)-propylammonium chloride, N,N-Dimethyl-N-(methoxycarbonyl)methyl-N',N'-dimethyl-N'-{3-(trimethoxysilyl)propyl}ethylene diammonium dichloride, N-Benzyl-N,N-dimethyl-N',N'-dimethyl-N'-{3-(trimethoxysilyl)propyl}ethylene diammonium dichloride, 3-{N-2(methoxycarbonylethyl)-N-3-(trimethoxysilyl)propyl}aminopropyldimethyl-(ethoxycarbonylmethyl)ammonium chloride, 3-{N-2-(methoxycarbonylethyl)-N-{3-(trimethoxysilyl)propyl}aminopropylbenzyldimethylammonium chloride, N,N,N-benzyldimethyl-N',N',N-benzyl-2-(methoxycarbonylethyl)-3-(trimethoxysilylpropyl)propylene-1,3-diammonium dichloride, 3-{N-2-(Methoxycarbonylethyl)-N-3-(trimethoxysilylpropyl){aminopropyldimethyl-5-(isopropoxycarbonylpentyl)ammonium chloride, 3-{N-2-(Methoxycarbonylethyl)-N-3-(trimethoxysilylpropyl)}aminopropyldimethylpentylammonium chloride, 3-{N-{3-(Methoxymethyl-3,3,3-trifluoropropylsilypropoxycarbonylethyl)}-N-{3-(trimethoxy silylpropyl)}}aminopropyldimethyl-5-(isopropoxycarbinylpentyl) ammonium chloride, 3-{N-{3-(Methoxymethyl-3,3,3-trifluopropropylsilypropoxycarbonylethyl)}-N-{3-(trimethoxysilylpropyl)}}aminopropyldimethyl-pentylammonium chloride, and 3-{N-{3-(Methoxymethyl-3,3,3-trifluoropropylsilypropoxycarbonylethyl)}-N-{3-(trimethoxysilylpropyl)}}-N',N'-dimethyl-amine-1,3.

Hereinafter and in the interest of simplicity, the foregoing quaternary ammonium compounds 1-10 will be referred to as Quats 1-10, respectively, and the formulas for such compounds are set forth hereinbelow and correspond to Quats 1-10 named above. Compound No. 11 is an intermediate for Quat Nos. 9 and 10. As noted hereinbefore, such novel compounds have utility as antimicrobially active agents.

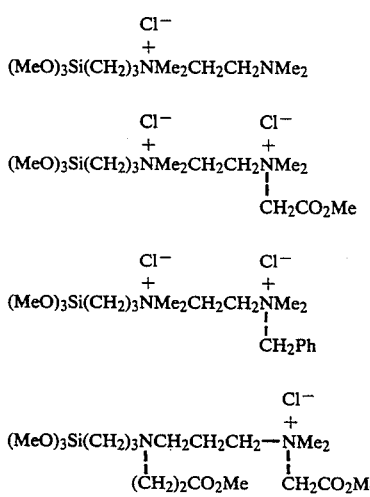

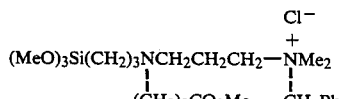

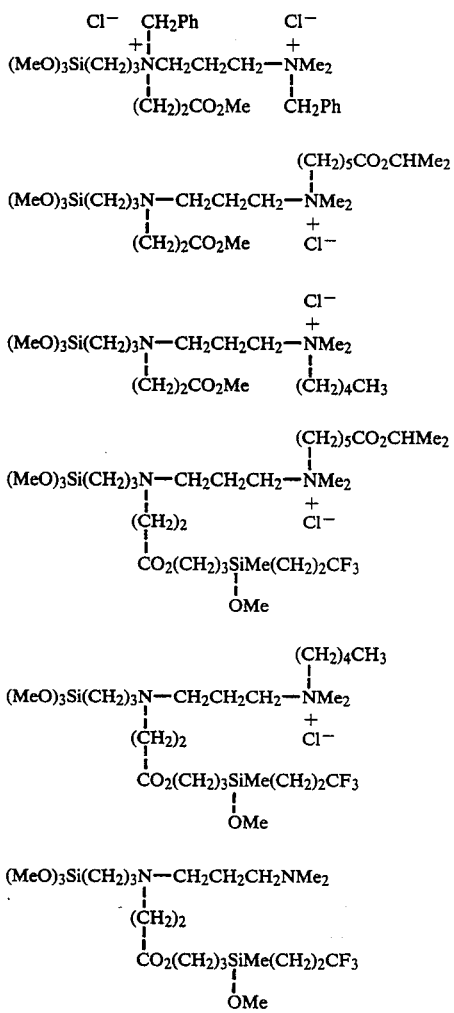

wherein Me is methyl and Ph is phenyl.

It is therefore an object of the present invention to provide a new series of quaternary ammonium salt compounds having biological activity.

These and other objects, features, and advantages of the herein defined invention will become readily apparent from the following detailed description of the present invention.

DETAILED DESCRIPTION

This invention relates to quaternary ammonium salt compounds possessing biological activity, and including di-quaternary amine salts and mono-quaternary amine salts as fifty percent solids in MeOH. These salts include combinations of ester, fluorocarbon, benzyl, amino, and alkyl, functionality. Di-quaternary ammonium salts of the general structure given in equation 1 were prepared.

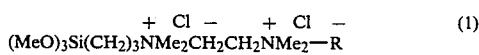

Mono-quaternary ammonium salts of the general structure shown in equation 2 were also prepared.

$$(MeO)_3Si(CH_2)_3N(CH_2)_3NMe_2-R \quad +Cl- \quad (2)$$
$$R$$

The preparation of the equation (1) compounds was initiated by refluxing in methanol two equivalents of 3-(trimethoxysilyl)propyl chloride, (hereinafter referred to as TMSPC), and one equivalent of N, N, N', N'-tetramethylethylenediamine to provide di-quaternary derivatives. The reaction resulted in Quat 1.

$$2 \, (MeO)_3Si(CH_2)_3Cl + Me_2NCH_2CH_2NMe_2 \longrightarrow \quad (3)$$
$$TMSPC$$
$$+$$
$$(MeO)_3Si(CH_2)_3NMe_2CH_2CH_2NMe_2 \xrightarrow{X}$$
$$1$$
$$+ \quad +$$
$$(MeO)_3Si(CH_2)_3NMe_2CH_2CH_2NMe_2(CH_2)_3Si(OMe)_3$$
$$12$$

The preparation of Quats 2-3 was carried out by refluxing Quat 1 in methanol with chloromethyl acetate and benzyl chloride as shown in equation 1 where R=CH$_2$CO$_2$Me and CH$_2$Ph, respectively. Amine "13" as a precursor was prepared as shown in equation 4.

$$(MeO)_3Si(CH_2)_3Cl + H_2N(CH_2)_3NMe_2 \xrightarrow{MeOH} \quad (4)$$
$$TMSPC$$
$$+HCl-$$
$$(MeO)_3Si(CH_2)_3NH(CH_2)_3NMe_2 \xrightarrow{NaOMe}{MeOH}$$
$$(MeO)_3Si(CH_2)_3NH(CH_2)_3NMe_2$$
$$13$$

A GC mass spectral (GCMS) analysis showed a first product peak to be Amine "13" and the second product peak to be a "bis-body" Amine "14" of equation 8.

$$(MeO)_3Si(CH_2)_3Cl + H_2N(CH_2)_3NMe_2 \xrightarrow{MeOH} \quad (5)$$
$$TMSPC$$
$$+HCl-$$
$$(MeO)_3Si(CH_2)_3NH(CH_2)_3NMe_2$$

$$+HCl- \quad (6)$$
$$(MeO)_3Si(CH_2)_3NH(CH_2)_3NMe_2 + H_2N(CH_2)_3NMe_2 \longrightarrow$$
$$+HCl-$$
$$(MeO)_3Si(CH_2)_3NH(CH_2)_3NMe_2 + H_2N(CH_2)_3NMe_2$$
$$13$$

$$(MeO)_3Si(CH_2)_3NH(CH_2)_3NMe_2 \xrightarrow{TMSPC} \quad (7)$$
$$13$$
$$+HCl-$$
$$\{(MeO)_3Si(CH_2)_3\}_2N(CH_2)_3NMe_2$$

$$+HCl- \quad \xrightarrow{H_2N(CH_2)_3NMe_2} \quad (8)$$
$$\{(MeO)_3Si(CH_2)_3\}N(CH_2)_3NMe_2$$
$$\{(MeO)_3Si(CH_2)_3\}N(CH_2)_3NMe_2$$
$$14$$
$$+$$
$$H_3N(CH_2)_3NMe_2$$
$$+Cl-$$

Amine "13" was reacted with methyl chloroacetate as outlined in equation 9.

$$(MeO)_3Si(CH_2)_3NH(CH_2)_3NMe_2 \xrightarrow[\substack{2. \, reflux \\ 3. \, base}]{1. \, ClCH_2R} \quad (9)$$
$$13$$
$$R$$
$$(MeO)_3Si(CH_2)_3N(CH_2)_3NMe_2$$
$$R = CO_2Me, Ph$$

A method of converting the secondary amino site to an amino site by Michael addition of the secondary amine to methyl acrylate was conducted, and the Michael addition of Amine "13" to methyl acrylate resulted in diamine 15 as seen in equation 10.

$$(MeO)_3Si(CH_2)_3NH(CH_2)_3NMe_2 \xrightarrow{CH_2=CHCO_2Me} \quad (10)$$
$$13$$
$$(MeO)_3Si(CH_2)_3N(CH_2)_3NMe_2$$
$$CH_2$$
$$CH_2CO_2Me$$
$$15$$

Five quat salt derivatives of diamine 15 were prepared. The derivative of methyl chloroacetate was prepared by mixing the amine and methyl chloroacetate, providing Quat 4 as a viscous syrup. Benzyl Quat 5 was prepared in a similar fashion from benzyl chloride. The benzyl quaternary salt was again prepared using a larger excess of benzyl chloride which resulted in more starting amine relative to benzyl chloride at the end of the reaction.

The reaction was continued by adding excess benzyl chloride to form di-quaternary ammonium Quat 6. A derivative of the diamine 15 and iso-propyl 6-chlorohexanoate was prepared in the manner noted above. The reaction provided Quat 7. Quat 8 was also prepared using n-pentyl chloride. Fluorine-containing derivatives of Amine "13" were also prepared. Allyl acrylate was reacted with 3-(3,3,3-trifluoro)propylmethoxymethylsilane using an activated platinum metal catalyst providing acrylate 16 shown in equation 11. The chlorosilane was treated with methanol containing an equivalent of triethyl amine resulting in methoxysilane 17.

$$CH_2=CHCO_2-CH_2CH=CH_2 + HSiCH_2CH_2CF_3 \xrightarrow{Pt} \quad (11)$$
$$\substack{Cl \\ Me}$$
$$Cl$$
$$CH_2=CO_2-CH_2CH_2CH_2SiCH_2CH_2CF_3 \xrightarrow{MeOH}{Et_3N}$$
$$16 \quad Me$$
$$OMe$$
$$CH_2=CO_2-CH_2CH_2CH_2SiCH_2CH_2CF_3$$
$$17 \quad Me$$

Starting amine and acrylate ester resulted in Michael adduct 11.

$$(MeO)_3Si(CH_2)_3NH(CH_2)_3NMe_2 \xrightarrow{17} \quad (12)$$
$$13$$
$$(MeO)_3Si(CH_2)_3N(CH_2)_3NMe_2$$
$$CH_2 \quad Me$$
$$CH_2CO_2(CH_2)_3SiOMe$$
$$CH_2$$
$$CH_2CF_3$$
$$11$$

The material was stripped of all volatile components and divided to make quaternary derivatives of iso-propyl-6-chlorohexanoate and n-pentyl chloride corresponding to Quat 9 and Quat 10, respectively.

The foregoing brief reaction sequence when taken in conjunction with the following detailed Examples, show that di-quaternary amines may be prepared by the reaction of 3-chloropropyltrimethoxysilane with tetramethylethylenediamine followed by methanol reflux with an appropriate halo compound. The foregoing also shows N,N-dimethyl-N'-{3-(trimethylsilyl)propyl}ethylenediamine to be a viable precursor to quaternary amines of varied functionality. Michael addition of amine hydrogen to acrylates is shown to be an effective method of incorporating diverse functionality. All of the quaternary salts and precursors were analyzed by nuclear magnetic resonance (NMR) spectroscopy and by IR spectroscopy and were consistent with the assigned structures.

EXAMPLE I

A. Synthesis of Quat 1

A stirred solution of 100 gm(0.504 mol) of TMSPC, 31.5 gm(0.272 mol) of tetramethylethylenediamine, and 64 gm of MeOH was charged to a 500 ml round bottom flask and heated to reflux. The reaction was monitored by GC which showed a decrease in starting materials up to 44 hours. After this time, the reaction was cooled to room temperature and excess reagents removed by rotary evaporation at 50° C. and 0.2 mm Hg. The resulting crystals of Quat 1 were added to 500ml portions of ether and washed to remove contaminates.

EXAMPLE II

B. Synthesis of Quat 2

A solution of 50 gm(0.158 mol) of Quat 1, 18.5 gm(0.17 mol) of methyl chloroacetate, and 30 gm of MeOH was charged to a 500 ml round bottom flask and heated to reflux with stirring. Reflux temperature was 71° C. The reaction was monitored by GC and after 21 hours no more decrease in the methyl chloroacetate occurred. A Dean-Stark take off tube was arranged and about 15 gm of methanol removed. The reflux temperature was increased to 77° C. for 3 hours. GC did not show additional decrease in the methyl chloroacetate but the reflux was continued for 4.5 hours longer and cooled to room temperature. The resulting compound was Quat 2.

EXAMPLE III

C. Synthesis of Quat 3

A solution of 50 gm(0.16 mol) of Quat 1, 40.6 gm(0.32 mol) of benzyl chloride, and 20 gm of MeOH was charged to a 500 ml round bottom flask and heated to reflux with stirring. The reaction was monitored by GC until about 50% of the benzyl chloride was consumed. GC showed the appearance of another peak identified by GCMS as benzyl methyl ether. The crude product was stripped of excess reagents by rotary evaporation yielding a pale yellow crystalline product. The crystals of Quat 3 were washed repeatedly with tetrahydrofuran (THF) and methanol to remove contaminates and the solvent was removed by rotary evaporation.

EXAMPLE IV

D. Synthesis of N,N-dimethyl-N'-(3-trimethoxysilylpropyl) propylenediamine-1,3 From N,N-Dimethylpropylenediamine and 3-Chloropropyltrimethoxysilane(TMSPC)

A stirred solution of 200 gm(1.01 mol) of TMSPC, 110 gm (1.08 M) of N,N-dimethylpropylenediamine, and 45 gm of MeOH was heated to reflux in a 1 liter flask and monitored by GC. After stirring overnight (ca. 28 hours), GC showed TMSPC was consumed affording a yellow viscous liquid. A small scale neutralization was carried out in a vial by shaking 5.5 gm of crude product with 0.9 gm of NaOMe in 6 ml of MeOH. GC and GC mass spectral (GCMS) analysis showed N,N-dimethyl-N'-(3-trimethoxysilylpropyl)propylenediamine-1,3 and N,N-bis(3-trimethoxysilylpropyl)-N',N'-dimethylpropylenediamine-1,3 in a 5:1 ratio. The remainder of the crude product was neutralized with 74 gm of NaOMe in 150 ml of MeOH for 0.5 hours at room temperature. The mixture was allowed to settle and the supernatant decanted for salts. Volatile components were removed by rotary evaporation leaving 188.4 gm of crude product which was flash bulb-to-bulb distilled between 117°-139° C./4 mm Hg and collected at −78° C. resulting in 93.2 gm( ca. 47% crude yield) The distillate was subjected to rotary evaporation at 80° C./0 5mm Hg to remove the remaining volatile components resulting in 50.1 gm of 84.4% GC area N,N-dimethyl-N'-(3-trimethoxyproply)propyenediamine(25.3% yield).

EXAMPLE IV - A

A solution of 218.4 gm(1.1 mol) of TMSPC, 277.0 gm(2.72 mol) of N,N-dimethylpropylenediamine, and 60.0 gm of MeOH were placed in a round bottom flask with a drying tube at ambient(27° C.) temperature. With stirring, the temperature spontaneously increased to 36° C. over 5 minutes and then began to cool. The stirred solution was heated to 99° C. GC analysis showed that the starting reagents were reacting to a new product. After 2.5 hours and at a temperature maximum of 103° C., GC showed no further change in the mixture. After cooling to 37° C., a slurry of 60.0 gm of NaOMe in 150 ml of MeOH was added to neutralize the amine hydrochloride. The temperature spontaneously increased to 47° C. and the mixture was stirred for 45 minutes and cooled to room temperature. Excess volatile components were removed by rotary evaporation resulting in 185.5 gm of residue which showed 91.6% N,N-dimethyl-N'-(3-trimethoxypropyl)propylenediamine and 5.2% N,N-bis(3-trimethoxypropyl)-N',N'-dimethyl-propylenediamine by GC. When the final product was allowed to stand at room temperature, a two phase mixture resulted. The top phase was N,N-dimethyl-N'-(3-trimethoxyproply)propyenediamine (NDTPD) and the bottom phase a MeOH and HCCl soluble polymer.

EXAMPLE IV - B

The above reaction was repeated with 481.2 gm(2.42 mol of TMSPC, 740.0 gm(7.26 mol) of N,N-dimethyl-propylenediamine, and 140 gm MeOH. The reaction was refluxed for 3 hours and cooled to room temperature. After removal of solvent. by rotary evaporation, NDTPD was obtained.

EXAMPLE V

E. Synthssis of Diamine 15.
N-3-(trimethoxysilyl)propyl-N-2-(methoxycarbonyl-)ethyl-dimethylpropylenediamine-1,3

To a 500 ml round bottom flask was charged a solution of 52.8 gm(0.2 mol of N,N-dimethyl-N'-{b 3- trimethoxysilyl)propyl}propylenediamine-1,3 and 52.0 gm(0.6 mol) of methyl acrylate and ca. 250 ppm w/w 2,6-dihydroxy-4-methylphenol (BHT). The solution was heated to reflux under air($Ca_2SO_4$ drying tube) for 4.5 hours and analyzed by GC which showed that the starting amine had been consumed and a product had formed. The crude mixture was stripped of volatile components by rotary evaporation at 40° C./5 mm Hg leaving 68.7 gm of diamine 15.

EXAMPLE VI - A

F. Synthesis of Quaternary Salts of Diamine 15

A 250 ml round bottom flask was fitted with a heating mantle, a magnetic stirrer, a thermometer, and a reflux condenser with a drying tube. To this was charged the reaction solution which was heated to reflux. From the reaction mixture was removed the volatile components by rotary evaporation at 60° C./4–8 mm Hg. The mixture was washed with solvent, and isolated as a viscous fluid.

EXAMPLE VI - B

1. Quaternization by Methyl Chloroacetate - Synthesis of Quat 4

A solution of 10.5 gm(0.03 mol) of diamine 15, 3.26 gm(0.03 mol) of methyl chloroacetate, and 20.0 gm of MeOH were charged to the flask. After refluxing for 3 hours, GC showed that the starting material had been consumed. A total of 13.5 gm(98% crude yield) of Quat 4 was obtained.

EXAMPLE VI - C

2. Quaternization by Benzyl Chloride - Synthesis of Quat 5

A solution of 10.5 gm(0.03 mol) of diamine 15, 4.0 gm(0.03 mol) of benzyl chloride, and 15 gm of MeOH were charged to the flask and heated to reflux. After 1.5 hours, GC showed 5-10% benzyl present along with amine. The reaction was allowed to reflux overnight(ca. 15 hr). GC showed the benzyl chloride consumed and some amine still present. Benzyl methyl ether was formed as a by-product of the reaction. Excess amine and other residue was removed by vigorous washing of the crude product in ether. After rotary evaporation, 10 gm(70% crude yield) of Quat 5 was obtained.

EXAMPLE VI - D

3. Quaternization by Two Equivalents of Benzyl Chloride - Synthesis of Quat 6

A solution of 10.5 gm(0.03 mol) of diamine 15, 10.0 gm(0.10 mol) total of benzyl chloride, and 40 gm of MeOH were heated at reflux for 92 hours which consumed all of the starting amine. Repeated washing with ether followed by rotary evaporation afforded Quat 6 as a white crystalline material.

EXAMPLE VI - E

4. Quaternization by iso-propyl 6-Chlorohexanoate - Synthesis of Quat 7

A solution of 10.5 gm(0.03 mol) of diamine 15, 6.2 gm(0.03 mol) of isopropyl 5-chlorohexanoate, and 10.0 gm of MeOH was charged to the flask and heated to reflux. After 90 hours, 1.0 gm(5 mmol) of isopropyl 3-chlorohexanoate was added to the mixture. At least 5% amine was present after refluxing 6 hours and the heating was stopped. The crude product was removed of volatiles by rotary evaporation and washed until all of the residue was removed leaving 15 gm(94%) of Quat 7.

EXAMPLE VI - F

5. Quaternization by Pentyl Chloride - Synthesis of Quat 8

A solution of 10.5 gm(0.03 mol) of diamine 15, 6.4 gm(0.06 mol) of pentyl chloride, and 5.0 gm of MeOH were charged to the flask and heated to reflux for 68 hours and concentrated by rotary evaporation. Repeated washing followed by rotary evaporation afforded 13.6 gm(99 g crude yield) of Quat 8.

EXAMPLE VII

G. Synthesis of 3-{1-{(3,3,3-Trifluoro)propyl}methoxymethylsilyl} propyl Acrylate, 17

To 30 gm(0.28 mol) of allyl acrylate containing 0.75 gm of an activated platinum metal catalyst, was added 3,3,3-trifluoropropyl)methylchlorosilane. The addition of the silane was carried out at 70° C. under 2% $O_2$/98% $N_2$ and the temperature did notexceed 75° C. When the addition was completed and the mixture had cooled to 44° C., 100 ml of MeOH containing 25 m(0.25 mol of $Et_3N$ was added in a dropwise fashion. White salts were formed. The salts were filtered and the crude product concentrated by rotary evaporation, redissolved in pentane. filtered, and the pentane removed by rotary evaporation at 50° C./4 mm Hg. The product was isolated by flash bulb-to-bulb distillation at 72° C./0.2–0.5 mm Hg and afforded 20 gm(25% yield) of Acrylate 17. Acrylate 17 was used in Example VIII.

EXAMPLE VIII

H. Michael Addition of Diamine 13 to Acrylate 17 - Synthesis of Diamine 11

A solution of 19.4 gm(0.07mol) of acrylate 17 and 18.0 gm(0.07 mol of diamine 13 were heated to reflux in a 250 ml round bottom flask for 17 hours at which time all of the acrylate had been consumed. To this refluxing mixture was added 3 gm(0.03 mol) of allyl acrylate which consumed the remaining amine after about 2 hours. After concentrating the crude product by rotary evaporation, the recovery was 36.4 gm(97%). This material was used in the next Example without further purification.

EXAMPLE IX

J. Quaternization of Diamine 11

1. Quaternization by iso-propyl 6-Chlorohexanoate - Synthesis of Quat 9

A solution of 17.6 gm(0.03 mol) of diamine 11, 8.0 gm(0.04 mol) of iso-propyl 6-chlorohexanoate, and 10.0 gm of MeOH was refluxed in a 250 ml round bottom flask for 140 hours and stripped of volatiles by rotary evaporation providing 23 gm(97%) of Quat 9.

2. Quaternization by Pentyl Chloride. Synthesis of Quat 10

A solution of 17.6 gm(0.03 mol) of diamine 11, 4.5 gm(0.04 mol) of pentyl chloride, and 10 gm of MeOH was refluxed in a 250 ml round bottom flask and stripped of volatiles by rotary evaporation providing 20 gm(95%) of Quat 10.

In order to demonstrate the durability and the substantivity of the compounds of the present invention, it should be noted that the anion of an aqueous sodium salt of bromphenol blue can be complexed with the cation of a polymerized silane of this invention while it is on a substrate. The blue colored complex, substantive to a water rinse, is qualitatively indicative of the presence of the cation on the substrate thus indicating the extent of antimicrobial agent on a given substrate. A comparison of the intensity of retained blue color to a color standard is used as a check to determine if the treatment has been applied properly.

The method consists of preparing a 0.02 to 0.04 weight percent solution of bromphenol blue in distilled water. This solution is made alkaline using a few drops of saturated $Na_2CO_3$ solution per 100 milliliters of the solution. Two to three drops of this solution are placed on the treated substrate and allowed to stand for two minutes. The substrate is then rinsed with copious amounts of tap water and the substrate is observed for a blue stain and it is compared to a color standard.

For a spectrophotometric determination, the following test is used.

The sodium salt of bromphenol blue is depleted from a standard solution by complexing with the cations on a treated substrate. The change in bromphenol blue concentration is determined spectrophotometrically or by comparison with color standards whereby the level of substrate treatment by the cationic silane is determinable.

The method consists of preparing a 0.02 weight percent standard solution of bromphenol blue in distilled water. It is made alkaline with a few drops of saturated $Na_2CO_3$ solution per 100 milliliters of bromphenol blue solution. The color of this solution is purple.

The blank solution is adjusted to yield a 10 to 12% transmittance reading when measured in 1 cm cells using a spectrophotometer set at 589 nm by the following method.

Fill a container 3/4 full of distilled water and add 2 ml of the 0.02% standard bromphenol blue solution for every 50 ml of distilled water. Add 0.5 ml of a 1 g Triton ® X-100 surfactant (manufactured by Rohm and Haas, Philadelphia, Pa., USA) aqueous solution for every 50 ml of water. Mix, and using the spectrophotometer, determine the maximum absorbance. Adjust the upper zero to 100% transmittance with distilled water. Check the percent transmittance of the working bromphenol blue solution at the maximum absorbance setting. Adjust the blank solution to 10 to 12% transmittance with either water or bromphenol blue standard solution as necessary.

The samples of treated substrate are tested by placing 0.5 gram samples of the substrate standards in a flask large enough for substantial agitation of the sample and the test solution. Add 50 ml of the working solution. Agitate for 20 minutes on a wrist-action shaker. Fill the test curvette with the test solution. Centrifuge if particulate matter is present. Measure the % transmittance at the wavelength set forth above. The transmittance is compared against a standard curve prepared by preparing several substrate samples of known concentration of the cationic silane. For example, samples containing a known amount of cationic silane at, for example, 0%, 0.25%, 0.50%, 0.75% and 1% are read spectrophotometrically and a curve is plotted.

The foregoing test was carried out for each compound at levels of 0.1%, 0.3%, and 0.5%, based on weight of fiber, and the surface was rayon. The results are tabulated in Table I below, and Series No. 1 indicates original as is treated fabric samples, whereas Series No. 2 indicates those same Series No. 1 original samples re-tested but only after having been subjected to a sodium dodecylbenzylsulfonate wash followed by an alcohol salt rinse and dried. Control samples of untreated rayon are also shown.

TABLE I

| Quat No. | Percent Transmittance | |
|---|---|---|
| | Series No. 1 | Series No. 2 |
| 1 | | |
| Control | 11.4 | 10.8 |
| 0.1% | 11.2 | 10.3 |
| 0.3% | 11.0 | 10.3 |
| 0.5% | 11.0 | 10.2 |
| 2 | | |
| Control | 11.4 | 10.8 |
| 0.1% | 11.0 | 10.5 |
| 0.3% | 11.5 | 9.8 |
| 0.5% | 14.2 | 9.9 |
| 3 | | |
| Control | 11.4 | 10.8 |
| 0.1% | 11.4 | 10.5 |
| 0.3% | 18.2 | 10.9 |
| 0.5% | 11.9 | 10.4 |
| 4 | | |
| Control | 11.4 | 11.2 |
| 0.1% | 11.1 | 11.2 |
| 0.3% | 11.2 | 11.7 |
| 0.5% | 11.5 | 11.0 |
| 5 | | |
| Control | 10.8 | 11.3 |
| 0.1% | 13.7 | 11.0 |
| 0.3% | 15.5 | 10.9 |
| 0.5% | 20.2 | 11.4 |
| 6 | | |
| Control | 10.8 | 10.9 |
| 0.1% | 16.7 | 11.3 |
| 0.3% | 22.1 | 11.0 |
| 0.5% | 42.9 | 10.6 |
| 7 | | |
| Control | 10.8 | 10.9 |
| 0.1% | 12.5 | 10.9 |
| 0.3% | 13.5 | 11.2 |
| 0.5% | 15.7 | 11.1 |
| 8 | | |
| Control | 11.4 | 10.8 |
| 0.1% | 11.2 | 10.3 |
| 0.3% | 11.8 | 9.9 |
| 0.5% | 12.2 | 10.4 |
| 9 | | |
| Control | 10.8 | 10.9 |
| 0.1% | 12.1 | 11.0 |
| 0.3% | 13.4 | 11.4 |
| 0.5% | 15.0 | 11.6 |
| 10 | | |
| Control | 10.8 | 11.3 |
| 0.1% | 11.9 | 11.6 |
| 0.3% | 13.0 | 11.3 |
| 0.5% | 15.2 | 11.5 |

In order to demonstrate the antimicrobial activity of the compounds of the present invention, the following test was conducted.

The antimicrobial activity of a rayon treated surface was evaluated by shaking a sample weighing 0.75 grams in a 750,000 to 1,500,000 count *Klebsiella pneumoniae* suspension for a one hour contact time. The suspension was serially diluted, both before and after contact, and cultured. The number of viable organisms in the suspensions was determined. The percent reduction based on the original count was determined. The method was intended for those surfaces havin a reduction capability of 75 to 100% for the specified contact time. The results are reported as the percent reduction.

Media used in this test were nutrient broth, catalog No. 0003-01-6 and tryptone glucose extract agar, catalog No. 0002-01-7 both available from Difco Laboratories, Detroit, Mich., U.S.A. The microorganism used was *Klebsiella pneumoniae* American Type Culture Collection; Rockville, Md. U.S.A., catalog No. 4352.

The procedure used for determining the zero contact time counts was carried out by utilizing two sterile 250 ml. screw-cap Erlenmeyer flasks for each sample. To each flask was added 70 ml of sterile buffer solution. To each flask was added, aseptically, 5 ml of the organism inoculum. The flasks were capped and placed on a wrist action shaker. They were shaken at maximum speed for 1 minute. Each flask was considered to be at zero contact time and was immediately subsampled by transferring 1 ml of each solution to a separate test tube containing 9 ml of sterile buffer. The tubes were agitated with a vortex mixer and then 1 ml of each solution was transferred to a second test tube containing 9 ml of sterile buffer. Then, after agitation of the tubes, 1 ml of each tube was transferred to a separate sterile petri dish. Duplicates were also prepared. Sixteen ml of molten (42° C.) tryptone glucose extract agar was added to each dish. The dishes were each rotated ten times clockwise and ten times counterclockwise. The dishes were then incubated at 37° C. for 24 to 36 hours. The colonies were counted considering only those between 30 and 300 count as significant. Duplicate samples were averaged. The procedure used for determining the bacterial count after 1 hour was essentially the same as that used to determine the count at the zero contact time. The only difference was that pour plating was performed at the and $10^0$ and $10^{-1}$ dilutions as well as at the $10^{-2}$ dilution "Percent reduction" was calculated by the formula $$\% R = \frac{\frac{B+C}{2} - A}{\frac{B+C}{2}} 100$$

where A is the count per milliliter for the flask containing the treated substrate; B is zero contact time count per milliliter for the flask used to determine "A" before the addition of the treated substrate and C is zero contact time count per milliliter for the untreated control substrate.

The foregoing test was carried out for each compound at levels of 0.1%, 0.3%, and 0.5%, based on weight of fiber. As noted above, the surface was rayon. The results are tabulated in Table II below, and Series No. 1 indicates original as is treated fabric samples, whereas Series No. 2 indicates those same Series No. 1 original samples re-tested but only after having been subjected to the foregoing durability treatment. Control samples of untreated rayon are also shown.

TABLE II

| Quat No. | Percent Reduction | |
|---|---|---|
| | Series No. 1 | Series No. 2 |
| 1 | | |
| Control | 48.3 | 60.9 |
| 0.1% | 73.5 | 40.9 |
| 0.3% | 89.9 | 53.0 |
| 0.5% | 94.4 | 71.0 |
| 2 | | |
| Control | 47.7 | 60.9 |
| 0.1% | 80.1 | 62.0 |
| 0.3% | 94.2 | 56.4 |
| 0.5% | 98.8 | 58.8 |
| 3 | | |
| Control | 50.5 | 60.9 |
| 0.1% | 91.0 | 53.7 |
| 0.3% | 99.6 | 61.3 |
| 0.5% | 99.9 | 75.4 |
| 4 | | |
| Control | — | 55.4 |
| 0.1% | 73.5 | 53.5 |
| 0.3% | 79.4 | 37.6 |
| 0.5% | 92.3 | 58.4 |
| 5 | | |
| Control | 46.4 | 64.9 |
| 0.1% | 96.5 | 75.6 |
| 0.3% | 99.7 | 67.8 |
| 0.5% | 100.0 | 80.5 |
| 6 | | |
| Control | 53.0 | 47.5 |
| 0.1% | 99.8 | 56.7 |
| 0.3% | 100.0 | 71.4 |
| 0.5% | 100.0 | 74.1 |
| 7 | | |
| Control | 42.7 | 47.5 |
| 0.1% | 99.7 | 70.1 |
| 0.3% | 100.0 | 74.0 |
| 0.5% | 100.0 | 95.1 |
| 8 | | |
| Control | 49.2 | 60.9 |
| 0.1% | 72.9 | 62.7 |
| 0.3% | 99.2 | 63.3 |
| 0.5% | 99.9 | 78.5 |
| 9 | | |
| Control | 45.6 | 47.5 |
| 0.1% | 99.8 | 70.5 |
| 0.3% | 100.0 | 82.6 |
| 0.5% | 100.0 | 93.7 |
| 10 | | |
| Control | 50.6 | 64.9 |
| 0.1% | 97.9 | 59.4 |
| 0.3% | 99.6 | 87.0 |
| 0.5% | 100.0 | 90.8 |

The compounds of the present invention are useful in applications where the reduction in number or elimination of microorganisms on a surface or other material is desired.

It will be apparent from the foregoing that many other variations and modifications may be made in the structures, compounds, compositions, and methods described herein without departing substantially from the essential features and concepts of the present invention. Accordingly, it should be clearly understood that the forms of the invention described herein are exemplary only and are not intended as limitations on the scope of the present invention.

That which is claimed is:

1. A compound selected form the group consisting of compounds having the general formulae:

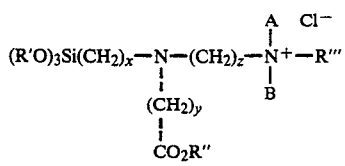 (I)

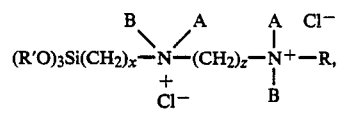 (II)

and

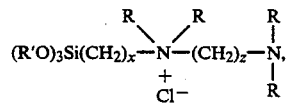 (III)

wherein
- A and B are each independently selected from methyl, ethyl, and propyl radicals;
- R' is selected from methyl, ethyl, propyl, iso-propyl, and butyl radicals;
- R" is selected from benzyl, $CF_3(CF_2)_x-$, $CH_{18}H_{37}$, $CF_3(CH_2)_x-$, $-(CH_2)_xSiR'_u(OR')_vR$, alkyl, alkenyl, aryl, and arylalkyl radicals;
- R'" is $CH_2-G$ wherein
  - G is selected from R', R", ethers, ketones, esters, or $CO_2R$ groups;
- u has a value of from 0 to 2;
- v has a value of from 0 to 2 with the proviso that u+v cannot exceed 2;
- x has a value of from 0to 18;
- y has a value of 2;
- z has a value of from 2 to 18; and
- R is selected from R', R", or R'".

2. A compound of the formula

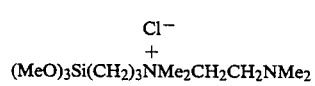

wherein Me is methyl.

3. A compound of the formula

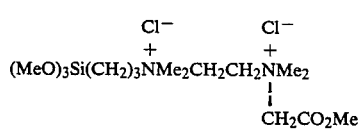

wherein Me is methyl.

4. A compound of the formula

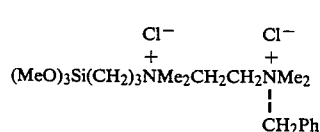

wherein Me ismethyl and Ph is phenyl.

5. A compound of the formula

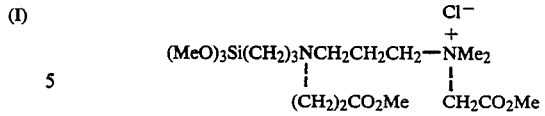

wherein Me is methyl.

6. A compound of the formula

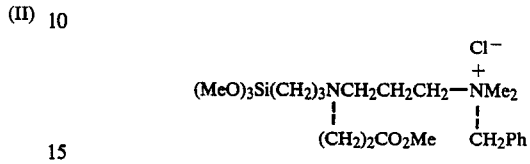

wherein Me is methyl and Ph is phenyl.

7. A compound of the formula

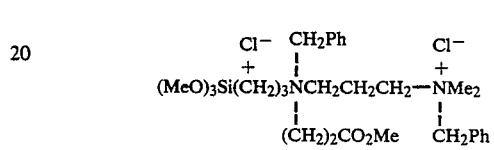

wherein Me is methyl and Ph is phenyl.

8. A compound of the formula

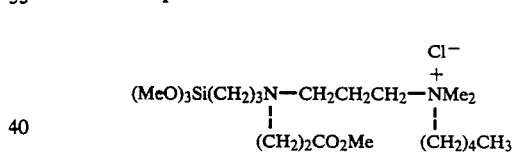

wherein Me is methyl.

9. A compound of the formula

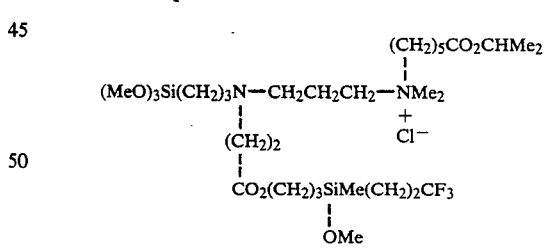

wherein Me is methyl.

10. A compound of the formula

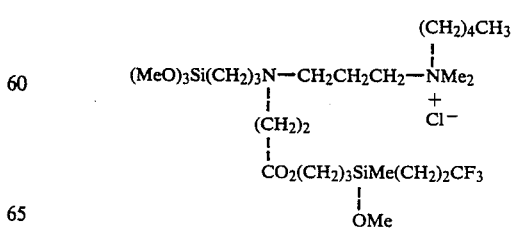

wherein Me is methyl.

11. A compound of the formula

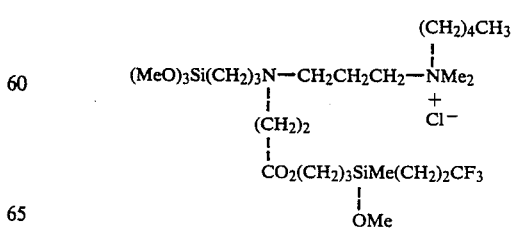

wherein Me is methyl.

* * * * *